United States Patent [19]

Hirai et al.

[11] Patent Number: 4,525,180

[45] Date of Patent: Jun. 25, 1985

[54] PROCESS FOR RECOVERY OF ETHYLENE FROM GASEOUS MIXTURE

[75] Inventors: Hidefumi Hirai; Makoto Komiyama; Susumu Hara, all of Tokyo, Japan

[73] Assignee: Hidefumi Hirai, Tokyo, Japan

[21] Appl. No.: 590,417

[22] Filed: Mar. 15, 1984

[30] Foreign Application Priority Data

Mar. 19, 1983 [JP] Japan .................................. 58-46163
Jul. 16, 1983 [JP] Japan ................................ 58-129785

[51] Int. Cl.$^3$ ............................................. B01D 19/00
[52] U.S. Cl. ...................................... 55/37; 585/848; 585/849; 55/55
[58] Field of Search ................... 585/848, 849, 37, 55, 585/68

[56] References Cited

U.S. PATENT DOCUMENTS 3,592,865  7/1971  Long et al. ..................... 585/848 X
3,651,159  3/1972  Long et al. ........................... 585/848
3,927,176 12/1975  Turnbo et al. .................. 585/848 X Primary Examiner—Charles Hart
Attorney, Agent, or Firm—Cushman, Darby & Cushman

[57] ABSTRACT

With application of new liquid absorbent, comprised of a compound selected from a group composed of silver halide and cuprous halide, an aluminium halide, a polymer selected from a group composed of styrene and styrene derivatives, and an aromatic hydrocarbon, it is possible to recover ethylene by absorbing ethylene from gaseous mixture containing ethylene such as FCC off gas, ethylene plant off gas and coke oven gas. In particular, said liquid absorbent is neither diluted nor reduced its capability to absorb ethylene by water or its vapor contained in the said gaseous mixture, so the liquid absorbent can be used repeatedly for the recovery of ethylene from gaseous mixture containing ethylene and water or its vapor, without any pretreatment to reduce the water content of said gaseous mixture.

18 Claims, No Drawings

PROCESS FOR RECOVERY OF ETHYLENE FROM GASEOUS MIXTURE

BACKGROUND OF THE INVENTION

1. Field of the Invention

This invention relates to a process for recovery of ethylene from gaseous mixture containing ethylene by absorbing ethylene with liquid absorbent.

2. Description of the Prior Art

Ethylene is one of the most important basal raw materials in the chemical industry and can be obtained by the thermal cracking of such saturated hydrocarbons as natural gas, refinery gas and petroleum fractions. Whilst, it is well known that a considerable amount of ethylene is also contained in gases derived, as a by-product, from some kinds of cracking units or gasification units, for example, in FCC off gas, ethylene plant off gas or coke oven gas. Such gases, however, usually become available in the form of a gaseous mixture containing ethylene, carbon monoxide, nitrogen, oxygen, methane, ethane, carbon dioxide, hydrogen, etc. In addition, the gaseous mixture normally contains 1,000 to 20,000 ppm of water or its vapor. Consequently, it is required to separate ethylene from the gaseous mixture to utilize ethylene for chemical industry as a raw material.

Low temperature cryogenic separation is one of the process, which can obtain a large quantity of high purity ethylene, in which the gaseous mixture is cooled to liquefy C2 plus hydrocarbons therein and then thus liquefied hydrocarbons are fractionated at a low temperature ranging from $-95°$ to $-140°$ C. However, there are drawbacks that this process requires a complicated refrigerating and heat-recovery system and also high-grade materials for the equipment which result in a high erection cost and high utility consumption because the power requirement is large. It is further reported that water and carbon dioxide contained in the gaseous mixture causes some plugging troubles in the low-temperature piping system. Therefore, the process requires a pretreating system which can reduce the contents of water and carbon dioxide to less than 1 ppm.

Another process for the recovery of ethylene from a gaseous mixture containing ethylene is composed with the application of an appropriate absorbent. In U.S. patent specification No. 3,651,159, it is described that aluminium cuprous chloride solution which chloride forms a complex with ethylene is applicable for recovery of ethylene from ethylene-containing gas. However, the reaction in which the chloride is employed should preferably be run under substantially anhydrous conditions, e.g., less than about 10 ppm water. Therefore, this process also requires a pretreating system which can reduce the content of water to less than about 10 ppm.

SUMMARY OF THE INVENTION

The object of this invention is to provide a process for recovery of ethylene from a gaseous mixture containing, besides ethylene, one or more of gaseous components such as carbon monoxide, nitrogen, oxygen, ethane, methane, carbon dioxide, hydrogen, etc. Another object of this invention is to provide a process for recovery of ethylene from a gaseous mixture containing, besides said gaseous components, water or its vapor. A further object of this invention is to provide a process for the recovery of ethylene from a gaseous mixture containing water or its vapor, without any pretreatment for removal of water or its vapor from said gaseous mixture. A further object of this invention is to provide a process for recovery of ethylene from a gaseous mixture containing ethylene with repeated use of a liquid absorbent which is countercurrently contacted with said gaseous mixture in an absorber. A further object of this invention is to provide a process for recovery of ethylene from gaseous mixture containing ethylene under moderate operating conditions.

According to this invention, said object can be obtained with the application of a liquid absorbent, which is comprised of a compound selected from a group composed of silver halide and cuprous halide, an aluminium halide, a polymer selected from a group composed of polystyrene and polystyrene derivatives, and an aromatic hydrocarbon.

DETAILED DESCRIPTION OF THE PREFERRED EMBODIMENTS

The liquid absorbent, which is used in this invention, is comprised of a compound selected from a group composed of silver halide and cuprous halide, an aluminium halide, a polymer selected from a group composed of polystyrene and polystyrene derivatives, and an aromatic hydrocarbon. Each of these liquid absorbents can be easily prepared by dissolving a compound selected from a group composed of silver halide and cuprous halide, an aluminium halide, and a polymer selected from a group composed of polystyrene and polystyrene derivatives in an aromatic hydrocarbon, and by maintaining the mixture of these components at a temperature of higher than 20° C., preferably ranging from 40° to 80° C., for several hours while being stirred.

The first component to be used for the preparation of the liquid absorbent is a compound selected from a group composed of silver halide and cuprous halide, for example, silver chloride, silver fluoride, silver bromide, silver iodide, cuprous chloride, cuprous bromide and cuprous iodide.

The second component to be used for the preparation of the liquid absorbent is an aluminium halide, for example, aluminium chloride, aluminium fluoride, aluminium bromide, and aluminium iodide.

The third component to be used for the preparation of the liquid absorbent is a polymer selected from a group composed of polystyrene and polystyrene derivatives. This group includes polymers and copolymers of styrene and styrene derivatives. Styrene derivatives are, for example, alpha-methylstyrene, alpha-phenylstyrene, and stilbene. Styrene and styrene derivatives can be used as a homopolymer, or as a copolymer of each other, and also can be used as a copolymer with other polymeric monomers. The polymeric monomers which form a copolymer with styrene or styrene derivatives are, for example, propylene, 1-butene, isobutene, 3-methyl-1-butene, 1-pentene and vinylchloride. It is further possible to use dienes, for example, butadiene, isoprene and chloroprene, for copolymerization with styrene or styrene derivatives, if the unsaturated bond of such a copolymer is hydrogenated after copolymerization. Polymers and copolmers of styrene and styrene derivatives are, for example, polystyrene, polyalphamethylstyrene, styrene-propylene copolymer and styrene-vinylchloride copolymer. The content of styrene or styrene derivatives in these copolymers applicable for the preparation of the liquid absorbent of this invention is 10 to 99 mol-percent, preferably 30 to 90 mol-percent. The degree of polymerization of polymers or copolymers of styrene or styrene derivatives applicable for the preparation of the liquid absorbent of this invention ranges from 2 to 10,000, preferably from 4 to 3,000, and more preferably from 4 to 2,000, based on the aromatic residue (benzene nuclei) of styrene or styrene derivatives.

The fourth component to be used for the preparation of the liquid absorbent is an aromatic hydrocarbon, for example, benzene, toluene, xylene and chlorobenzene.

As for the composition of the liquid absorbents suitable for this invention, the molar ratio of silver halide or cuprous halide to aluminium halide is 0.5 to 2.0, preferably 1.0 to 1.5; the molar ratio of aromatic residue (benzene nuclei) of polystyrene or polystyrene derivatives to silver halide or cuprous halide is 0.3 to 30, preferably 1 to 5; and the molar ratio of aromatic hydrocarbon to silver halide or cuprous halide is 0.5 to 30, preferably 3 to 10.

The absorption of ethylene according to this invention can be carried out under atmospheric pressure, at a temperature ranging from $-40°$ to $90°$ C., preferably from $0°$ to $40°$ C. Of course, it can be carried out under a higher pressure. The ethylene can be desorbed either by heating the liquid absorbent, in which ethylene has been absorbed, at a temperature ranging from $40°$ to $140°$ C., preferably from $60°$ to $100°$ C., or by reducing the pressure of/over the liquid absorbent in which ethylene has been absorbed.

The liquid absorbent described above is more stable even though in the pressure of water or its vapor in the gaseous mixture. As can be seen from Example 1, 2, 5 and 6, the absorbing capability of ethylene is almost stable even after the repeated absorption and desorption of ethylene in the system that gaseous mixture containing about 0.6 mol-percent of water, corresponding to 6,000 ppm of water vapor is employed as feed gas. This means that according to this invention, a pretreating system for the reduction of the contents of water or its vapor in the gaseous mixture is unnecessary, provided that a gaseous mixture with a saturated vapor pressure of water is employed as the feed gas.

On the contrary, as is shown in Comparative Example 1 and 3, the absorbent without polystyrene or polystyrene derivatives, that is to say, a liquid absorbent composed of silver halide or cuprous halide, aluminium halide and aromatic hydrocarbon only, decreases its capability to absorb ethylene, if the absorbent comes into contact with gaseous mixtures containing water or its vapor.

A further notable thing of the liquid absorbent with silver halide as the first component of the liquid absorbent of this invention is almost not absorb carbon monoxide. Consequently, when such a liquid absorbent is applied to the gaseous mixture containing carbon monoxide in it, it is possible to recover ethylene without the co-absorption of carbon monoxide. Liquid absorbent with cuprous halide has not such an effect as this.

EXAMPLE 1

Silver chloride belonging to special reagent grade was used without any refining. Aluminium chloride belonging to special class grade reagent was used after being dehydrated and refined by a vaccum sublimation method. Toluene belonging to the first class grade reagent was used after being dehydrated with metallic sodium, and then distilled. Pellet-like reagent grade straight-chain polystyrene having 1,600 to 1,800 degree of polymerization was used after refined three times by a reprecipitation method with a chloroform-methanol solvent, and then dried in vaccum at $60°$ C. for 12 hours. Ethylene gas contained in a bomb was used, and it was prepared beforehand so as to contain 0.6 mol-percent water, corresponding to 6,000 volume ppm water vapor. 99.999 percent pure nitrogen gas contained in a bomb was used, and it was dried with a packed column of Molecular Sieve 3A just before use.

Under the dried nitrogen atmosphere, 8.24 g (57.5 m mol) silver chloride, 6.97 g (52.3 m mol) aluminium chloride and 5.44 g (corresponding to 52.3 m mol aromatic residue) straight-chain polystyrene were put into a 100 ml two-necked eggplant type flask covered with aluminium foil. 50 ml toluene was added to the flask, then the contents of the flask were heated and maintained at $80°$ C. for 4 hours while being stirred with a magnetic stirrer to prepare a liquid absorbent.

The liquid absorbent was cooled to $20°$ C. The two-necked eggplant type flask holding the liquid absorbent was connected to a vessel holding 2,980 ml of gaseous mixture composed of ethylene containing 0.6 mol-percent water vapor and nitrogen under 1 atm. (0.94 atm. ethylene and 0.6 atm. nitrogen) to make the absorbent to absorb ethylene. For 3 minutes at the initial period of absorption, the gaseous mixture was circulated over the liquid absorbent with an air pump. The amount of ethylene absorbed was measured by the gas burette method at $20°$ C. Ethylene was rapidly absorbed—After 3 minutes, 18.3 m mol ethylene, corresponding to 32 mol-percent of charged silver chloride, was absorbed, and after 60 minutes, 24.7 m mol ethylene, corresponding to 43 mol-percent of charged silver chloride, was absorbed.

The liquid absorbent which had absorbed ethylene was heated at $100°$ C. under 1 atm., while a spiral reflux condenser fitted to the two-necked eggplant type flask being cooled with tap water, to desorb the absorbed ethylene. The amount of ethylene desorbed was 23.3 m mol. After cooling of the liquid absorbent which desorbed ethylene to $20°$ C., the flask holding the liquid absorbent was connected to a vessel holding 2,980 ml of the aforesaid gaseous mixture to make the absorbent to absorb ethylene. For 3 minutes at the initial period of absorption, the gaseous mixture was circulated over the liquid absorbent with an air pump. Ethylene was rapidly absorbed—After 3 minutes, 17.5 m mol ethylene, corresponding to 30 mol-percent of charged silver chloride, was absorbed, and after 60 minutes, 24.7 m mol ethylene, corresponding to 43 mol-percent of charged silver chloride, was absorbed.

This example indicates that after contacting the liquid absorbent with the gaseous mixture containing 5640 ppm water vapor (6,000 ppm $\times$ 0.94), the rate of absorption and the amount of ethylene absorbed were almost same.

EXAMPLE 2

The same reagents as used in Example 1 were also used in this example.

Under the dried nitrogen atmosphere, 3.30 g (23.0 m mol) silver chloride, 3.07 g (23.0 m mol) aluminium chloride and 2.40 g (corresponding to 23.0 m mol aromatic residue) straight-chain polystyrene were put into a 100 ml two-necked eggplant type flask covered with aluminium foil. 23 ml toluene was added to the flask, then the contents of the flask were heated and maintained at $50°$ C. for 4 hours while being stirred with a magnetic stirrer to prepare a liquid absorbent. Except that this liquid absorbent contained the equimolecular quantities of silver chloride and aluminium chloride, it was prepared in the same manner as that of Example 1.

The liquid absorbent was cooled to 20° C. The two-necked eggplant type flask holding the liquid absorbent was connected to a vessel, holding 2,980 ml of gaseous mixture of the same composition as employed in Example 1, to make the absorbent to absorb ethylene. For 3 minutes at the initial period of absorption, the gaseous mixture was circulated over the liquid absorbent with an air pump. Ethylene was rapidly absorbed—After 3 minutes, 9.2 m mol ethylene, corresponding to 39 mol-percent of charged silver chloride, was absorbed, and after 60 minutes, 11.4 m mol ethylene, corresponding to 49 mol-percent of charged silver chloride, was absorbed.

The liquid absorbent which had absorbed ethylene was heated at 100° C. under 1 atm., while a spiral reflux condenser fitted to the two-necked eggplant type flask being cooled with tap water, to desorb the absorbed ethylene.

After cooling of the liquid absorbent thus regenerated to 20° C., the flask holding the liquid absorbent was connected to a vessel holding 2,980 ml of the aforesaid gaseous mixture to make the absorbent to absorb ethylene. For 3 minutes at the initial period of absorption, the gaseous mixture was circulated over the liquid absorbent with an air pump. Ethylene was rapidly absorbed—After three minutes, 10.2 m mol ethylene, corresponding to 44 mol-percent of charged silver chloride, was absorbed, and after 60 minutes, 11.4 m mol ethylene, corresponding to 49 mol-percent of charged silver chloride, was absorbed.

Once again, the liquid absorbent which has absorbed ethylene was heated at 100° C. under 1 atm., in the same manner as described above, to desorb the absorbed ethylene. After cooling of the liquid absorbent which desorbed ethylene to 20° C., the flask holding the liquid absorbent was connected to a vessel holding 2,980 ml of aforesaid gaseous mixture to make the absorbent to absorb ethylene in the same manner as described above. Ethylene was rapidly absorbed—After 3 minutes, 8.9 m mol ethylene, corresponding to 38 mol-percent of charged silver chloride, was absorbed, and after 60 minutes, 11.6 m mol ethylene, corresponding to 50 mol-percent of charged silver chloride, was absorbed.

This example also indicates that after contacting the liquid absorbent with the gaseous mixture containing 5,640 ppm water vapor, the rate of absorption and the amount of ethylene absorbed were almost same.

COMPARATIVE EXAMPLE 1

The same reagents as used in Example 1 were also used in this comparative example.

Under the dried nitrogen atmosphere, 3.17 g (22.1 m mol) silver chloride, 2.95 g (22.1 m mol) aluminium chloride were put into a 100 ml two-necked eggplant type flask covered with aluminium foil. 22 ml toluene was added to the flask, then the contents of the flask were heated and maintained at 50° C. for 4 hours while being stirred with a magnetic stirrer to prepare a liquid absorbent. Except that this liquid absorbent did not contain polystyrene, it was prepared in the same manner as that of Example 2.

The liquid absorbent was cooled to 20° C. The two-necked eggplant type flask holding the liquid absorbent was connected to a vessel holding 2,980 ml of gaseous mixture composed of ethylene containing 0.6 mol-percent water vapor and nitrogen under 1 atm. (0.94 atm. ethylene and 0.06 atm. nitrogen) to make the absorbent to absorb ethylene. For 3 minutes at the initial period of absorption, the gaseous mixture was circulated over the liquid absorbent with an air pump. The amount of ethylene absorbed was measured by the gas burette method at 20° C. Ethylene was rapidly absorbed—After 3 minutes, 8.9 m mol ethylene, corresponding to 40 mol-percent of charged silver chloride, was absorbed, and after 60 minutes, 11.3 m mol ethylene, corresponding to 51 mol-percent of charged silver chloride, was absorbed.

The liquid absorbent which had absorbed ethylene was heated at 100° C. under 1 atm., while a spiral reflux condenser fitted to the two-necked eggplant type flask being cooled with tap water, to desorb the absorbed ethylene. After cooling of the liquid absorbent thus regenerated to 20° C., the flask holding the liquid absorbent was connected to a vessel holding 2,980 ml of aforesaid gaseous mixture to make the absorbent to absorb ethylene. For 3 minutes at the initial period of absorption, the gaseous mixture was circulated over the liquid absorbent with an air pump. Ethylene was rapidly absorbed—After 3 minutes, 8.1 m mol ethylene, corresponding to 36 mol-percent of of charged silver chloride, was absorbed, and after 60 minutes, 9.9 m mol ethylene, corresponding to 45 mol-percent of charged silver chloride, was absorbed. The absorbing capability of this liquid absorbent without polystyrene decreased by 13 percent, as a result of its contact with the gaseous mixture containing 5,640 ppm water vapor.

Once again, the liquid absorbent which had absorbed ethylene was heated at 100° C. under 1 atm., in the same manner as described above, to desorb the absorbed ethylene. After cooling of the liquid absorbent thus regenerated to 20° C., the flask holding the liquid absorbent was connected to a vessel holding 2,980 ml of the aforesaid gaseous mixture to make the absorbent to absorb ethylene. For 3 minutes at the initial period of absorption, the gaseous mixture was circulated over the liquid absorbent with an air pump. Ethylene was rapidly absorbed—After 3 minutes, 7.8 m mol ethylene, corresponding to 35 mol-percent of charged silver chloride, was absorbed, and after 60 minutes, 8.6 m mol ethylene, corresponding to 39 mol-percent of charged silver chloride, was absorbed. The absorbing capability of this liquid absorbent without polysturene decreased further by 13 percent, as a result of its contact with the gaseous mixture containing 5,640 ppm water vapor.

EXAMPLE 3

The same reagents as used in Example 1 were also used in this example.

Under the dried nitrogen atmosphere, 5.32 g (37.1 m mol) silver chloride, 4.95 g (37.1 m mol) aluminium chloride and 3.87 g (corresponding to 37.1 m mol aromatic residue) straight-chain polystyrene were put into a 100 ml two-necked eggplant type flask covered with aluminium foil. 37 ml toluene was added to the flask, then the contents of the flask were heated and maintained at 50° C. for 4 hours while being stirred with a magnetic stirrer to prepare a liquid absorbent. That is, this liquid absorbent was prepared in the same manner as that of Example 2.

The liquid absorbent was cooled to 20° C. 99.95 percent pure carbon monoxide contained in a bomb was used, it was dried with a packed column of Molecular Sieve 3A just before use. The two-necked eggplant type flask holding the liquid absorbent was connected to a vessel, holding 2,980 ml of gaseous mixture composed of carbon monoxide and nitrogen under 1 atm. (0.94 atm. carbon monoxide and 0.06 atm. nitrogen) to make the absorbent to absorb carbon monoxide. For 3 minutes at the initial period of absorption, the gaseous mixture was circulated over the liquid absorbent with an air pump. The amount of carbon monoxide absorbed was measured by the gas burette method at 20° C. The amount of carbon monoxide absorbed after 120 minutes was 0 ml. That is, carbon monoxide was not absorbed by this liquid absorbent at all.

EXAMPLE 4

A liquid absorbent, composed of 5.32 g (37.1 m mol) silver chloride, 4.95 g (37.1 m mol) aluminium chloride and 3.87 g (corresponding to 37.1 m mol aromatic residue) of straight-chain polystyrene and 37 ml toluene was prepared by a similar procedure as described in Example 1.

The liquid absorbent was cooled to 16° C. Nitrogen gas, which was saturated with water vapor at 16° C. (water content: 5.5 percent), was introduced into a 100 ml two-necked eggplant type flask holding the liquid absorbent at a flow rate of 50 ml/second for one minute, while the liquid absorbent being stirred with a magnetic stirrer. The water content of the nitrogen gas was analyzed by gas chromatography (Polapack Q column, 2 m, 60° C.). The water content of the nitrogen gas, which passed through over the liquid absorbent, was 5.5 percent. The water content of the nitrogen gas was almost never reduced after its contact with the liquid absorbent.

COMPARATIVE EXAMPLE 2

A liquid absorbent, composed of 5.32 g (37.1 m mol) silver chloride, 4.95 g (37.1 m mol) aluminium chloride and 37 ml toluene was prepared by a similar procedure as described in Example 1. Except that this liquid absorbent did not contain 3.87 g polystyrene, it is the same as the liquid absorbent used in Example 4.

The liquid absorbent was cooled to 16° C. Nitrogen gas, which was saturated with water vapor at 16° C. (water content: 5.5 percent), was introduced into a 100 ml two-necked eggplant type flask holding the liquid absorbent at a flow rate of 50 ml/second for one minute, while the liquid absorbent being stirred with a magnetic stirrer. The water content of the nitrogen gas was analyzed by gas chromatography. The water content of the nitrogen gas, which passed through over the liquid absorbent, was 0.1 percent. The water content of the nirogen gas was remarkably reduced after its contact with this liquid absorbent.

EXAMPLE 5

Cuprous chloride belonging to special class grade reagent was used after it was repreciptitated with hydrochloric acid diluted by water, washed consecutively with ethanol and ether, and dried in vaccum at 80° C. for 12 hours. The other reagents and gases were refined in the same manner as those of Example 1.

A liquid absorbent, composed of 2.26 g (22.8 m mol) cuprous chloride, 3.04 g (22.8 m mol) aluminium chloride, 2.81 g (corresponding to 27.0 m mol aromatic residue) straight-chain polystyrene and 15 ml toluene was prepared by a similar precedure as described in Example 1.

The liquid absorbent was cooled to 25° C. A two-necked eggplant type flask holding the liquid absorbent was connected to a vessel holding 2,980 ml of gaseous mixture composed of ethylene containing 0.6 mol-percent water and nitrogen under 1 atm. (0.94 atm. ethylene and 0.06 atm. nitrogen) to make the absorbent to absorb ethylene. For 3 minutes at the initial period of absorption, the gaseous mixture was circulated over the liquid absorbent with an air pump. The amount of ethylene absorbed was measured by the gas burette method at 25° C. Ethylene was rapidly absorbed—After 3 minutes, 28.6 m mol ethylene, corresponding to 125 mol-percent of charged cuprous chloride, was absorbed, and after 60 minutes, 34.8 m mol ethylene, corresponding to 152 mol-percent of charged cuprous chloride, was absorbed.

The liquid absorbent which had absorbed ethylene was heated at 70° C. under 1 atm., while a spiral reflux condenser fitted to the two-necked eggplant type flask being cooled with tap water, to desorb the absorbed ethylene. Ethylene was rapidly desorbed and after 10 minutes, the amount of ethylene desorbed was 22.5 m mol. After cooling of the liquid absorbent which desorbed ethylene to 25° C., the flask holding the liquid absorbent was connected to a vessel holding 2,980 ml of the aforesaid gaseous mixture to make the absorbent to absorb ethylene. For 3 minutes at the initial period of absorption, the gaseous mixture was circulated over the liquid absorbent with an air pump. Ethylene was rapidly absorbed—After three minutes, 18.2 m mol ethylene, corresponding to 80 mol-percent of charged cuprous chloride, was absorbed, and after 60 minutes, 22.3 m mol ethylene, corresponding to 98 mol-percent of charged cuprous chloride, was absorbed.

Once again, the liquid absorbent which had absorbed ethylene was heated at 70° C. under 1 atm., in the same manner as described above, to desorb the absorbed ethylene. After cooling of the liquid absorbent which desorbed ethylene to 25° C., the flask holding the liquid absorbent was connected to a vessel holding 2,980 ml of aforesaid gaseous mixture to make the absorbent to absorb ethylene in the same manner as described above. Ethylene was rapidly absorbed—After 3 minutes, 16.2 m mol ethylene, corresponding to 71 mol-percent of charged cuprous chloride, was absorbed, and after 60 minutes, 22.9 m mol ethylene, corresponding to 100 mol-percent of charged cuprous chloride, was absorbed.

The absorption and desorption of ethylene were repeated further three times in the same manner as described above, and the rate of absorption and the amount of ethylene absorbed were approximately the same as those in the second and the third absorptions. This example indicates that after contacting the the liquid absorbent with the gaseous mixture containing 5,640 ppm water vapor, the rate of absorption and the amount of ethylene absorbed were almost same.

EXAMPLE 6

The same reagents as used in Example 5 were also used in this example.

A liquid absorbent, composed of 2.51 g (25.3 m mol) cuprous chloride, 3.38 g (25.3 m mol) aluminium chloride, 2.64 g (corresponding to 25.4 m mol aromatic residue) straight-chain polystyrene and 25 ml toluene was prepared by a similar procedure as that of Example 5.

The liquid absorbent was cooled to 25° C. A two-necked eggplant type flask holding the liquid absorbent was connected to a vessel holding 2,980 ml of gaseous mixture composed of ethylene containing 0.6 mol-percent water vapor and nitrogen under 1 atm. (0.94 atm. ethylene and 0.06 atm. nitrogen) to make the absorbent to absorb ethylene. For 3 minutes at the initial period of absorption, the gaseous mixture was circulated over the liquid absorbent with an air pump. Ethylene was rapidly absorbed—After 3 minutes, 22.9 m mol ethylene, corresponding to 90 mol-percent of charged cuprous chloride, was absorbed, and after 60 minutes, 37.1 m mol ethylene, corresponding to 146 mol-percent of charged cuprous chloride, was absorbed.

The liquid absorbent which had absorbed ethylene was heated at 100° C. under 1 atm., while a spiral reflux condenser fitted to the two-necked eggplant type flask being cooled with tap water, to desorb the absorbed ethylene. After cooling of the liquid absorbent which desorbed ethylene to 25° C., the flask holding the liquid absorbent was connected to a vessel holding 2,980 ml of the aforesaid gaseous mixture to make the absorbent to absorb ethylene in the same manner as described above. Ethylene was rapidly absorbed—After 3 minutes, 19.4 m mol ethylene, corresponding to 76 mol-percent of charged cuprous chloride, was absorbed, and after 60 minutes, 37.9 m mol ethylene, corresponding to 149 mol-percent of charged cuprous chloride, was absorbed.

Once again, the liquid absorbent which had absorbed ethylene was heated at 100° C. under 1 atm., in the same manner as described above, to desorb the absorbed ethylene. After cooling of the liquid absorbent which desorbed ethylene to 25° C., the flask holding the liquid absorbent was connected to a vessel holding 2,980 ml of aforesaid gaseous mixture to make the absorbent to absorb ethylene in the same manner as described above. Ethylene was rapidly absorbed—After 3 minutes, 20.5 m mol ethylene, corresponding to 81 mol-percent of charged cuprous chloride, was absorbed, and after 60 minutes, 37.4 m mol ethylene, corresponding to 148 mol-percent of charged cuprous chloride, was absorbed.

The absorption and desorption of ethylene were repeated further three times in the same manner as described above, and the rate of absorption and the amount of ethylene absorbed were approximately the same as those in the second and the third absorptions. This example indicates that after contacting the liquid absorbent with the gaseous mixture containing 5640 ppm water vapor, the rate of absorption and the amount of ethylene absorbed were almost same.

COMPARATIVE EXAMPLE 3

The same reagents as used in Example 5 were also used in this example.

A liquid absorbent, composed of 1.99 g (20.1 m mol) cuprous chloride, 2.26 g (20.1 m mol) aluminium chloride and 25 ml toluene was prepared by the similar procedure as that of Example 5.

The liquid absorbent was cooled to 23° C. A two-necked eggplant type flask holding the liquid absorbent was connected to a vessel holding 2,980 ml of gaseous mixture composed of ethylene containing 0.6 mol-percent water vapor and nitrogen under 1 atm. (0.94 atm. ethylene and 0.06 atm. nitrogen) to make the absorbent to absorb ethylene. For 3 minutes at the initial period of absorption, the gaseous mixture was circulated over the liquid absorbent with an air pump. The amount of ethylene absorbed was measured by the gas burette method at 23° C. Ethylene was rapidly absorbed—After 3 minutes, 26.5 m mol ethylene, corresponding to 132 mol-percent of charged cuprous chloride, was absorbed, and after 60 minutes, 33.4 m mol ethylene, corresponding to 166 mol-percent of charged cuprous chloride, was absorbed.

The liquid absorbent which had absorbed ethylene was heated at 100° C. under 1 atm., while a spiral reflux condenser fitted to the two-necked eggplant type flask being cooled with tap water, to desorb the absorbed ethylene. After cooling of the liquid absorbent which desorbed ethylene to 23° C., the flask holding the liquid absorbent was connected to a vessel holding 2,980 ml of the aforesaid gaseous mixture to make the absorbent to absorb ethylene in the same manner as described above. Ethylene was rapidly absorbed—After 3 minutes, 23.3 m mol ethylene, corresponding to 116 mol-percent of charged cuprous chloride, was absorbed, and after 60 minutes, 31.3 m mol ethylene, corresponding to 156 mol-percent of charged cuprous chloride, was absorbed. The absorbing capability of this liquid absorbent without polystyrene decreased by 6 percent, as a result of its contact with the gaseous mixture containing 5,640 ppm water vapor.

Once again, the liquid absorbent which had absorbed ethylene was heated at 100° C. under 1 atm., in the same manner as described above, to desorb the absorbed ethylene. After cooling of the liquid absorbent which desorbed ethylene to 23° C., the flask holding the liquid absorbent was connected to a vessel holding 2,980 ml of aforesaid gaseous mixture to make the absorbent to absorb ethylene in the same manner as described above. Ethylene was rapidly absorbed—After 3 minutes, 21.7 m mol ethylene, corresponding to 108 mol-percent of charged cuprous chloride, was absorbed, and after 60 minutes, 29.7 m mol ethylene, corresponding to 148 mol-percent of charged cuprous chloride, was absorbed. The absorbing capability of the liquid absorbent without polystyrene decreased further by 5 percent, as a result of its contact with the gaseous mixture containing 5,640 ppm water vapor.

The absorption and desorption of ethylene were repeated further three times in the same manner as described above, and the amount of ethylene absorbed after 60 minutes were 27.9 m mol, 26.1 m mol, and 24.2 m mol, corresponding to 139, 130 and 120 mol-percent of charged cuprous chloride respectively. The absorbing capability of the liquid absorbent without polystyrene decreased gradually by 5, 6 and 6 percent each time as a result of its contact with the gaseous mixture containing 5,640 ppm water vapor.

EXAMPLE 7

A liquid absorbent, composed of 5.25 g (36.6 m mol) silver chloride, 4.44 g (33.3 m mol) aluminium chloride, 3.46 g (corresponding 33.3 m mol aromatic residue) straight-chain polystyrene and 35 ml toluene was prepared by a similar procedure as described in Example 1.

The liquid absorbent was cooled to 20° C. A two-necked eggplant type flask holding 2,980 ml of gaseous mixture composed of dried ethylene and nitrogen under 1 atm. (0.94 atm. ethylene and 0.06 atm. nitrogen) to make the absorbent to absorb ethylene. For 3 minutes at the initial period of absorption, the gaseous mixture was circulated over the liquid absorbent with an air pump. The amount of ethylene absorbed was measured by the gas burette method at 20° C. Ethylene was rapidly absorbed—After 3 minutes, 11.3 m mol ethylene, corresponding to 31 mol-percent of charged silver chloride, was absorbed, and after 60 minutes, 15.6 m mol ethylene, corresponding to 43 mol-percent of charged silver chloride, was absorbed.

The liquid absorbent which had absorbed ethylene was heated at 100° C. under 1 atm., while a spiral reflux condenser fitted to the two-necked eggplant type flask being cooled with tap water, to desorb the absorbed ethylene. Ethylene was rapidly desorbed and the amount of ethylene desorbed was 15.2 m mol. After cooling of the liquid absorbent which desorbed ethylene to 20° C., the flask holding the liquid absorbent was connected to a vessel holding 2,980 ml of the aforesaid gaseous mixture to make the absorbent to absorb ethylene. For 3 minutes at the initial period of absorption, the gaseous mixture was circulated over the liquid absorbent with an air pump. Ethylene was rapidly absorbed—After 3 minutes, 11.0 m mol ethylene, corresponding to 30 mol-percent of charged silver chloride, was absorbed, and after 60 minutes, 15.2 m mol ethylene, corresponding to 42 mol-percent of charged silver chloride, was absorbed.

EXAMPLE 8

A polymer of styrene, the degree of polymerization of which is 2 to 8 (molar ratio of the polymer having the degree of polymerization 2, 3, 4, 5, 6, 7 and 8 were 16, 27, 23, 16, 10, 5 and 3 percent respectively) was used. The other reagents and gases were refined in the same manner as those of Example 1.

Under the dried nitrogen atmosphere, 6.89 g (48.1 m mol) silver chloride, 6.41 g (48.1 m mol) aluminium chloride and 5.0 g (corresponding to 48.1 m mol aromatic residue) of said polymer of styrene were put into a 100 ml two-necked eggplant flask covered with aluminium foil. 50 ml toluene was added to the flask, then the contents of the flask were heated and maintained at 50° C. for 4 hours while being stirred with a magnetic stirrer to prepare a liquid absorbent.

The liquid absorbent was cooled to 20° C. The two-necked eggplant type flask holding the liquid absorbent was connected to a vessel holding 2,980 ml of gaseous mixture composed of ethylene containing 0.6 mol-percent water and nitrogen under 1 atm. (0.94 atm. ethylene and 0.06 atm. nitrogen) to make the absorbent to absorb ethylene. For 3 minutes at the initial period of absorption, the gaseous mixture was circulated over the liquid absorbent with an air pump. The amount of ethylene absorbed was measured by the gas burette method at 20° C. Ethylene was rapidly absorbed—after 3 minutes, 20.2 m mol ethylene, corresponding to 42 mol-percent of charged silver chloride, was absorbed, and after 60 minutes, 24.1 m mol ethylene, corresponding to 50 mol-percent of charged silver chloride, was absorbed.

The liquid absorbent which had absorbed ethylene was heated at 100° C. under 1 atm., while a spiral reflux condenser fitted to the flask being cooled with tap water, to desorb the absorbed ethylene. After cooling of the liquid absorbent which desorbed ethylene to 20° C., the flask holding the liquid absorbent was connected to a vessel holding 2,980 ml of the aforesaid gaseous mixture to make the absorbent to absorb ethylene. For 3 minutes at the initial period of absorption, the gaseous mixture was circulated over the liquid absorbent with an air pump. Ethylene was rapidly absorbed—after 3 minutes, 21.2 m mol ethylene, crresponding to 44 mol-percent of charged silver chloride, was absorbed, and after 60 minutes, 23.6 m mol ethylene, corresponding to 49 mol-percent of charged silver chloride, was absorbed.

This example indicates that after contacting the liquid absorbent with the gaseous mixture containing 5,640 ppm water vapor, the rate of absorption and the amount of ethylene absorbed were almost same.

What is claimed is:

1. A process for recovery of ethylene from a gaseous mixture containing ethylene and water or water vapor, said process comprising selectively absorbing ethylene to the exclusion of water or water vapor with a liquid absorbent comprised of a compound selected from the group consisting of silver halide and cuprous halide, an aluminium halide, a polymer selected from the group consisting of polystyrene and polystyrene derivatives, and an aromatic hydrocarbon.

2. The process of claim 1 wherein ethylene is absorbed by said liquid absorbent at low temperature, including the additional step of regenerating said liquid absorbent which has absorbed ethylene by heating the liquid absorbent to desorb the ethylene absorbed, and thus regenerating the liquid absorbent for repeated use to absorb ethylene from a gaseous mixture containing ethylene.

3. The process of claim 2 wherein ethylene is absorbed at a temperature ranging from 40° to 90° C.

4. The process of claim 2 wherein the liquid absorbent which has absorbed ethylene is heated at a temperature ranging from 40° to 140° C. to desorb the ethylene absorbed.

5. The process of claim 1 wherein ethylene is absorbed by the liquid absorbent under the pressure of said gaseous mixture, the additional step of regenerating the liquid absorbent by then reducing the pressure of the liquid absorbent or over the liquid absorbent in which ethylene has been absorbed so as to desorb the ethylene which has been absorbed by the liquid absorbent, and thus regenerating the liquid absorbent for repeated use to absorb ethylene from gaseous mixture containing ethylene.

6. The process of claim 1 wherein said halide is chloride.

7. The process of claim 1 wherein said polymer is polystyrene.

8. The process of claim 1 wherein said aromatic hydrocarbon is benzene or toluene.

9. The process of claim 1 wherein said gaseous mixture additionally contains carbon monoxide, the liquid absorbent selectively absorbs ethylene to the exclusion of carbon monoxide, and said liquid absorbent contains a silver halide.

10. The process of claim 1 wherein said gaseous mixture is a gaseous mixture containing carbon monoxide and said compound selected from a group composed of silver halide and cuprous halide is a silver halide.

11. The process of claim 1 wherein said gaseous mixture contains from 1 to 55,000 ppm water or water vapor.

12. The process of claim 11 wherein said gaseous mixture contains from 1 to 6,000 ppm water or water vapor.

13. The process of claim 9 wherein said gaseous mixture contains from 1 to 55,000 ppm water or water vapor.

14. The process of claim 13 wherein said gaseous mixture contains from 1 to 6,000 ppm water or water vapor.

15. The process of claim 1 wherein said polystyrene or polystyrene derivative has the degree of polymerization of 4 to 3,000.

16. The process of claim 15 wherein said polystyrene or polystyrene derivative has the degree of polymerization of 4 to 2,000.

17. The process of claim 9 wherein said polystyrene or polystyrene derivative has the degree of polymerization of 4 to 3,000.

18. The process of claim 17 wherein said polystyrene or polystyrene derivative has the degree of polymerization of 4 to 2,000.

* * * * *